United States Patent [19]
Rocha et al.

[11] Patent Number: 5,866,376
[45] Date of Patent: Feb. 2, 1999

[54] PRODUCTION OF OILY EMULSIONS MEDIATED BY A MICROBIAL TENSO-ACTIVE AGENT

[75] Inventors: Carlos Ali Rocha; Dosinda Gonzalez; Maria Lourdes Iturralde; Ulises Leonardo Lacoa, all of Caracas; Fernando Antonio Morales, Maracaibo, all of Venezuela

[73] Assignee: Universidad Simon Bolivar, Caracas, Venezuela

[21] Appl. No.: 806,884

[22] Filed: Feb. 25, 1997

[51] Int. Cl.$^6$ .......................... C12P 19/44; C07H 13/06; B01F 17/00

[52] U.S. Cl. .......................... 435/74; 435/100; 435/101; 536/4.1; 536/18.5; 536/123.13; 536/18.2; 252/351; 252/352; 252/354

[58] Field of Search .......................... 435/101, 74, 100; 536/4.1, 18.5, 123.13, 18.2; 252/351, 352, 354

[56] References Cited

U.S. PATENT DOCUMENTS

| | | | |
|---|---|---|---|
| 4,628,030 | 12/1986 | Kaeppelli et al. | 435/101 |
| 4,781,207 | 11/1988 | Balzer | 137/13 |
| 4,814,272 | 3/1989 | Wgner et al. | 435/74 |
| 4,923,483 | 5/1990 | Layrisse et al. | 44/51 |
| 4,933,281 | 6/1990 | Daniels et al. | 435/101 |
| 4,943,390 | 7/1990 | Hayes et al. | 252/355 |

OTHER PUBLICATIONS

Zhang et al., "Effect of rhamnolipid (biosurfactant) structure on solubilization and biodegradation of n–alkanes", Appl. Environ. Microbiol. 61 (6): 2247–15 (1995).

Schenk et al., "High–performance liquid chromatographic determination of the rhamnolipids produced by *Pseudomonas aeruginosa*", J. Chromatogr. 693 (1): 7–13 (1995).

McClure et al., "Effects of *Pseudomonas aeruginosa* rhamnolipids on human monocyte–derived macrophages", J. Leukocyte Biol. 51 (2): 97–102 (1992).

Zhang et al, Appl. Environ. Microbiol. 61(6):2247–2251 (1995).

Schenk et al, J. Chromatog. 693:7–13 (1995).

*Primary Examiner*—Francisco Prats
*Attorney, Agent, or Firm*—Pennie & Edmonds LLP

[57] ABSTRACT

The present invention is directed to biosurfactant stabilized emulsions of high viscosity hydrocarbons such as high viscosity crude oil wherein the biosurfactant is a metabolite of *Pseudomonas aeruginosa* (USB-CS1) and two methods for making the same. Preferably, the viscosity of the biosurfactant stabilized emulsions is below about 500 centipoise and, more preferably, below about 100 centipoise at ambient temperatures.

30 Claims, 8 Drawing Sheets

PRODUCTION OF OILY EMULSIONS MEDIATED BY A MICROBIAL TENSO-ACTIVE AGENT

FIELD OF THE INVENTION

The present invention is directed to emulsifying agents, emulsifying agent stabilized emulsions and methods for their preparation. More particularly, the present invention is directed to biosurfactants, to low viscosity biosurfactant stabilized emulsions of highly viscous hydrocarbons in water and to methods for preparing the same.

BACKGROUND OF THE INVENTION

Highly viscous hydrocarbons present viscosities from about 10,000 to about 500,000 centipoise (cp) at environmental or ambient temperatures (e.g., about 25° C.). Such hydrocarbons include American Petroleum Institute (API) viscous crude oil found in the U.S.A., Canada, China, Russia and Venezuela having, for example, an API value of about 13 degrees or less. The high viscosity of these hydrocarbons introduce several difficulties in their extraction, production, recovery, treatment and/or transportation.

For example, it is difficult to clean and remove residual viscous crude oil which has adhered to wall surfaces of large transport vessel tanks. The residual oil can amount to 5% or as much as 12 tons of oil from the original load, for example, of an oil tanker. Often large quantities of ballast water are used for cleaning and recovering the residual oil. Such recovery and cleaning methods are unappealing given the large quantities of oil and even larger quantities of oil contaminated cleaning water that is produced and then discharged. Thus, the use of water to clean and recover highly viscous residual oil from vessel tanks is both environmentally costly and economically inefficient.

Additionally, it is difficult to extract viscous crude oil from underground sources. Further, because of the high viscosity, transportation of highly viscous crude oil from production fields to refineries or to ports via pipelines becomes extremely difficult. For economically successful extraction, production, recovery, convenient transportation and/or subsequent treatment of highly viscous hydrocarbons, it is necessary that the viscosity of the fluid be reduced, preferably, not to exceed about 500 cp and, more preferably, about 100 cp at operating or ambient temperatures. Further, it is also necessary that the highly viscous hydrocarbons have a reduced pressure drop, preferably, of less than or equal to about 20 psi/mile when transported in a well conduit or a pipeline.

To achieve these pressure drop and viscosity levels, conventional techniques such as heating, dilution with solvents, annular transportation, watery lubrication and encapsulation, have either failed or are too costly. Further, various emulsifying agents along with water have been used to emulsify and effect the viscosity of highly viscous hydrocarbons. However, these emulsification techniques have met with little success in solving the aforesaid problems.

An emulsion is a dispersed system containing at least two immiscible liquid phases. In an emulsion, one immiscible phase forms droplets that are internally dispersed in the second immiscible phase. The second immiscible phase constitutes the continuous phase of the emulsion. It is generally believed that due to excess free energy associated with the surface of the droplets present therein, emulsions are inherently thermodynamically unstable. To minimize the excess free energy, the dispersed droplets, therefore, intrinsically strive to come together and reduce their surface area. If unabated, the droplets floccuolate, ultimately coalesce, grow in size and decrease in number until one large drop is formed. Eventually, the dispersed droplets coalesce or fuse to the degree that the emulsion is substantially destroyed. In effect, the emulsion phases are substantially separated into relatively distinct bulk phases. As non-dispersed bulk phases, one phase of the original emulsion has a minimum of its surface area that is in contact with that of the second phase wherein minimization of the surface free energy is satisfied.

In order to reduce the inherent tendency to coalesce or fuse, an emulsifying agent is added to the immiscible phases to improve emulsion stability. It is generally believed that an emulsifying agent forms a film around each or nearly each dispersed droplet in an emulsion. It is further believed that an emulsifying agent is adsorbed at least as a monolayer at an interface between, for example, a first phase and a second phase. However, the film can be a monolayer, a multi-layer, or a collection of small particles adsorbed at the interface between the phases (i.e., dispersed phase and continuous phase) forming a barrier.

Further, it is likewise believed that the presence of a well-developed charge on the droplet surface significantly aids in promoting the stability of the droplet due to repulsion between approaching drops. Such a potential is more likely to be present when a charged or ionized emulsifying agent is used.

Additionally, it is believed that, by forming a film (or the like) around the dispersed phase of an emulsion, an emulsifying agent lowers the interfacial tension between the emulsion phases and, thereby, lowers the surface free energy of the emulsion. In effect, by lowering the emulsion surface free energy, the emulsifying agent serves to maintain the surface area of the dispersed phase. As a consequence, the emulsifying agent retards and/or eliminates the inherent tendency of the dispersed droplets to coalesce and increases the emulsion stability.

Biosurfactants are a class of emulsifying agents made by microorganisms. Various biosurfactants are produced by microorganisms such as yeasts, fungi, algae and bacteria which yield extracellular metabolites having emulsifying properties. For example, biosurfactant producing microorganisms of the "lipotrehalose" type are Arthrobacter, Brevivacterium, Mycobacterium Kansai, M. Fortuitum, Corynebacterium Diptheriae and Nocardia Esteorides. These microorganisms excrete a metabolite which is a biosurfactant. Typically, the emulsifying agent metabolites have two functional groups, one hydrophilic and the other hydrophobic. The hydrophilic and hydrophobic functional groups increase the metabolite concentrations at the interface between two immiscible phases.

Generally, biosurfactants are classified according to their chemical nature which depends largely upon the genetic make-up of the organism that produced such biosurfactant as well as the culture medium in which the organism was incubated to produce the biosurfactant (e.g., extracellular metabolites, also referenced as bioemulsifiers). By traditional mutagenesis, by genetic engineering and/or by varying the culture medium it is possible to obtain new tensoactive emulsifying agents. For example, it is possible to use recombinant DNA and immobilization techniques to form useful, novel, substantially or relatively non-toxic tensoactive agents for the oil industry.

Some biosurfactants are of a lipo-peptidic and phospholipidic nature. Other biosurfactants have a glucolipidic nature. That is, lipids associated to sugars such as trehalose, soforose, rhamnose, diglycosyl diglycerides and other polysaccharides. The presence of such biosurfactants at the interface effect properties such as surface tension, interfacial tension, density, viscosity, electrical conductivity and osmotic pressure. Further, since the chemical structure of biosurfactants is, typically, complex in comparison to synthetic surfactants (which tend to be simple and highly repetitive structures), biosurfactants have the advantage of being able to emulsify, for example, liquid phases with long and ramified chains (e.g., highly viscous API crude oil). Most importantly, such metabolites stabilize and induce emulsions between immiscible phases.

Some of the desirable properties of an emulsifying agent are that the agent should (1) be surface-active and reduce surface tension, (2) be adsorbed, preferably readily and quickly, around dispersed drops as a condensed, non-adherent film which prevents or reduces droplet coalescence, (3) impart to the droplets an adequate electrical potential so that mutual repulsion occurs between droplets of the emulsion, (4) effect the viscosity of the emulsion (e.g., lower the viscosity of the emulsion below that of the most viscous phase) (5) be effective in a reasonably low concentration (e.g., critical micellar concentration) (6) be useful at a low economic cost and (7) be useful at a low environmental cost. However, not all emulsifying agents possess these properties or to the same degree.

For example, fatty alcohols from whale sperm and other less expensive triglycerides (such as coconut oil) have been used as raw materials to produce emulsifying agents. However, these agents produce excessive foam, are difficult to dissolve, require the use of undesirable non-aqueous toxic solvents, are slow to biodegrade and exhibit undesirable toxicity due in part to solvent toxicity.

Furthermore, in terms of the rheological behavior of emulsions, it is often difficult to predict the effect of emulsifying agents upon the viscosity of bulk liquid phases as well as upon the resultant emulsion. This is particularly true because emulsions are difficult systems to study. For example, under shear forces, the droplets of an internal dispersed phase are subject to deform which can unpredictably effect the rheology of the emulsion. Further, with respect to rheology, because of unpredictable interactions between the emulsifying agent, the internal dispersed phase and the continuous phase of the emulsion, it is not possible to make apriori determinations of the rheological effects of an emulsifying agent on an emulsion.

With reference to viscous hydrocarbons, if extraction, recovery, production, transportation and subsequent treatment of highly viscous crude oil from underground sources were made more economically and more environmentally feasible (e.g., cost effective), the benefits would be substantial for countries such as the United States, Canada, China, Russia, Venezuela and other locations where large deposits remain untapped. Thus, it is desirable to form a novel bio-emulsifier and to form a low viscosity emulsion (stabilized with the novel bio-emulsifier) of highly viscous hydrocarbons (e.g., highly viscous crude oil) with water to facilitate economical extraction, production, recovery, treatment and/or transportation thereof. It is further desirable to form a low viscosity emulsion of highly viscous crude oil with water wherein the low viscosity emulsion is formed at a lower economic and lower environmental cost than heretofore possible with conventional techniques.

SUMMARY OF THE INVENTION

It is therefore an object of the present invention (1) to provide a stable, low cost, environmentally friendly emulsifying agent, (2) to provide an emulsion (stabilized with such emulsifying agent) of a highly viscous hydrocarbon such as viscous API crude oil (e.g., of 13 or less degrees API) for the benefits attendant therewith and (3) to provide methods for making the emulsifying agent and emulsion.

It is therefore another object of the present invention to provide a stable, low viscosity emulsion of high viscosity hydrocarbons with water to economically facilitate their product, extraction, combustion, and/or transportation via, for example, a conduit or pipeline and to provide a method for making the same.

It is therefore a further object of the present invention (1) to provide a biosurfactant, (2) to provide a stable, low viscosity emulsion of highly viscous crude oil, water and the biosurfactant wherein the emulsion has a viscosity of less than or equal to about 500 cp and which emulsion, preferably, exhibits a pressure drop not greater than about 20 psi/mile and (3) to provide methods for making the same.

The biosurfactant of the present invention is preferably produced by a process which comprises the steps of:

(a) inoculating a culture medium containing nitrogen, enzyme co-factor(s) and an organic carbon source with at least one biosurfactant producing microorganism of the *Pseudomonas aeruginosa* strain designated USB-CS1;

(b) incubating the microorganism in the culture for an incubation period and at an incubation temperature sufficient to produce at least a critical micellar concentration of the biosurfactant; and (c) sterilizing the incubated culture with humid heat.

Further, according to the present invention, the biosurfactant comprises a rhamnolipid of formula (I):

wherein or mixtures thereof, wherein n, m, p and q are integers, wherein n=6, p=6, m=1 and q=1 and wherein $A^+$ is a cation or H. Preferably, the compound is in its anionic form.

The emulsion of the present invention comprises: a mixture of (a) a high viscosity hydrocarbon having a viscosity between about 10,000 cp to about 500,000 cp at about 25° C.; and (b) a solution of a rhamnolipid biosurfactant wherein the emulsion has a viscosity of less than or equal to about 500 cp at about 25° C.

Preferably, the emulsion has a pressure drop of no greater than about 20 psi/mile in a pipeline transporting the emulsion. Even more preferably, the emulsion has a viscosity less than or equal to about 100 cp at about 25° C.

According to the present invention, the emulsion of high viscosity hydrocarbon and water is made by the process comprising the steps of:

(a) providing a solution of a rhamnolipid biosurfactant, which is present in at least a critical micellar concentration; and (b) mixing the solution with a high viscosity hydrocarbon having a viscosity between about 10,000 to about 500,000 cp at about 25° C.

Thus, the solution contains a sufficient amount of the biosurfactant to form a stable emulsion having a viscosity of less than or equal to about 500 cp at about 25° C.

DETAILED DESCRIPTION OF THE PREFERRED EMBODIMENTS

For convenience, the terms bio-emulsifier, tenso-active agent, biosurfactant, emulsifier and emulsifying agent are used interchangeably herein. As is recognized by those skilled in the art, the term "critical micellar concentration" means the lowest surfactant concentration at which the formation of micelles occurs.

The emulsifying agents of the present invention are rhamnolipid biosurfactants. These rhamnolipids have been isolated from *Pseudomonas aeruginosa* (USB-CS1), grown in different sources of carbon such as glucose, petroleum, kerosene, glycerol, peptone, etc. This type of biosurfactant is formed by two units of fatty acids (3-hydroxydecanoic acid) wherein the hydroxyl portion of the first acid is condensed with the carboxyl portion of the second acid, with one free hydroxyl group remaining. The free hydroxyl is condensed with at least one rhamnose molecule. Further, the emulsifying agents of the present invention are preferably anionic. Anionic emulsifying agents may be formed, for example, of a long hydrocarbon chain having an anionic functional group such as $SO_4^{2-}$ or $COO^-$ (e.g. rhamnolipid of formula (I)). According to the present invention, two types of rhamnolipids with emulsifying properties have been formed. A first type, formula (I), supra, wherein X=a rhamnose sugar, is formed by two rhamnose and two fatty acid molecules and a second type, formula (I), supra, wherein X=H, is formed by one rhamnose molecule and two fatty acid molecules.

In accordance with the present invention, rhamnolipids of formula (I), supra, effect a decrease in the water surface tension from about 72 dynes/cm to about 30 dynes/cm and a decrease in the interfacial tension (relative to kerosene) from about 16 dynes/cm to about 0.25–3 dynes/cm with light (about 25 or more API degrees), medium (from about 14 to about 25 API degrees), heavy (about 13 API degrees or less) and extra-heavy oil in a watery medium, respectively. Further, the rhamnolipids of the present invention are (1) less expensive, (2) more biodegradable, (3) readily alterable to be useful with a wide spectrum of immiscible phases (4) better able to reduce the viscosity of highly viscous hydrocarbons and (5) relatively non-toxic (e.g., low toxicity or non-toxic) than other surfactants (e.g., synthetic surfactants), respectively.

As previously noted, the process for forming the biosurfactants of the present invention comprises the steps of:

(a) inoculating a culture medium containing nitrogen, enzyme co-factors and an organic carbon source with a dose of inoculant containing at least one biosurfactant producing microorganism, said microorganism being a strain of *Pseudomonas aeruginosa* (USB-CS1);

(b) incubating said microorganism in said culture for an incubation period and at an incubation temperature sufficient to produce at least a critical micellar concentration of said biosurfactant; and (c) sterilizing said incubated culture with humid heat.

The biosurfactant producing microorganism of the present invention is *Pseudomonas aeruginosa* designated as USB-CS1 for convenience. A deposit of this strain (USB-CS1) of *Pseudomonas aeruginosa* was made on Dec. 26, 1996 at the following depository: American Type Culture Collection (Rockville, Md.). The deposit is identified by accession number ATCC 55925.

The culture medium suitable for use with the present invention includes any suitable culture medium for *Pseudomonas aeruginosa*. The culture medium contains nitrogen and/or a source thereof, enzyme co-factor(s) and/or source(s) thereof and organic carbon and/or a source thereof. For example, a suitable culture medium for growth of *Pseudomonas aeruginosa* (USB-CS1; ATCC 55925) contains glucose (1.5% w/v; from Merck), yeast extract (0.5% w/v; from DiFco or Hi-Media) and peptone (0.5% w/v; from DiFco or Hi-Media) based on a total volume of the culture medium so formed (hereinafter referred to as a commercial culture medium). Another suitable culture medium is the minimum defined culture medium (MMPB). MMPB contains, for example, glucose (1.5% w/v), urea (0.05% w/v), $MgSO_4$ (0.0005% w/v) and $K_2HPO_4$ (0.2% w/v) based on a total volume or MMPB.

For *Pseudomonas aeruginosa* (USB-CS1), commercially available culture media provide a rich growth medium compared to MMPB. Commercial culture media allow greater amounts of biosurfactant production for each percent (i.e, % v/v) of initial inoculant used compared to that achieved in MMPB. On the other hand, the MMPB allows a higher amount of biosurfactant produced by each cell of USB-CS1 compared to that achieved in commercial culture media. However, due to lower overall population growth of *Pseudomonas aeruginosa* (USB-CS1) cells from the initial dose of inoculant in MMPB versus that in a commercial culture medium the overall amount of biosurfactant produced in MMPB is less than that produced using a commercial culture medium. However, when one projects costs for large scale production, since commercial culture media are more expensive than MMPB, MMPB is preferred.

Nitrogen or sources thereof suitable for use with the present invention include, but are not limited to, peptone, yeast extract, urea or mixtures thereof. Other suitable nitrogen sources are well know in the art (to which the present invention pertains) and may be used. However, urea is preferred. The concentration of the nitrogen should be sufficient to allow proper incubation and growth of USB-CS1 to produce a sufficient amount of the biosurfactant of the present invention. A sufficient amount of the biosurfactant is an amount equal to or greater than the critical micellar concentration (CMC) thereof. A suitable concentration of urea in the culture medium is, for example, from about 0.01% by weight/volume (w/v) to about 0.1% by weight/volume (w/v). All weight/volume (w/v) percents noted herein are based on the total volume of the culture medium. Preferably, the concentration of urea is about 0.05% (w/v). However, the concentration of peptone, yeast extract or mixtures thereof in the culture medium is from about 0.05% (w/v) to about 1.5% (w/v) preferably, about 0.5% (w/v).

The enzyme co-factor(s) suitable for use with the present invention include a source of $Mg^{++}$ and a source of phosphorous such as $MgSO_4$ and $K_2HPO_4$, respectively. Other suitable sources of $Mg^{++}$ and phosphorous are well known in the art and may be used. The concentration of the $MgSO_4$ enzyme co-factor and the phosphorous co-factor should be sufficient to allow proper incubation and growth of *P. aeruginosa* USB-CS1 to produce a sufficient amount of the biosurfactant (e.g., at least CMC) of the present invention. In the commercially available culture media, the enzyme co-factor(s) are provided therein, for example, in any yeast extract that may be included. However, the MMPB, the enzyme co-factor(s) need to be separately added. In MMPB, for example, the concentration of $MgSO_4$ is from about 0.0001 (w/v) to about 0.01% (w/v), preferably, about 0.0005% (w/v). Further in MMPB, for example, the concentration of $K_2HPO_4$ is from about 0.05% (w/v) to about 0.5% (w/v), preferably, about 0.2% (w/v). The culture medium (e.g., commercial medium or MMPB etc.) may contain other minerals (e.g., trace minerals) necessary for the proper incubation and growth of *Pseudomonas aeruginosa* (e.g., USB-CS1) that are know in the art. The mineral concentrations present in the culture medium are sufficient to form at least a critical micellar concentration of the biosurfactant of the present invention.

The organic carbon or sources thereof suitable for use with the present invention include, but are not limited to, glucose from any source, peptone from any source, yeast extract from any source or mixtures thereof. Other suitable organic carbon sources are well known in the art and may be used. The concentration of the organic carbon source should be sufficient to allow proper incubation and growth of USB-CS1 to produce a sufficient amount of the biosurfactant (e.g., at least CMC) of the present invention. For example, the concentration of the glucose in the culture medium is from about 0.5% (w/v) to about 1.5% (w/v). However, 1.5% (w/v) of glucose is preferred. For peptone and/or yeast extract, when used as the organic carbon source, their concentration is from about 0.05% (w/v) to about 1.5% (w/v), preferably, about 0.5% (w/v). Further, other additives may be present in the culture medium in amount that are necessary for the incubation and growth of *Pseudomonas aeruginosa* (e.g., USB-CS1) which are know to those skilled in the art to which the present invention pertains.

The dose of the inoculant (*P. aeruginosa* USB-CS1) introduced into the culture medium for incubation should be sufficient to promote growth of the *Pseudomonas aeruginosa* and be sufficient to produce a sufficient amount of the biosurfactant (e.g., at least CMC) of the present invention. For example, the amount of the inoculant is from about 0.1% by volume/volume (v/v) to about 9.0% by volume/volume (v/v), based on the total volume of the culture medium. However, a concentration of 1.0% (v/v) of the inoculant is preferred. This concentration is equivalent to about 2.5 grams of USB-CS1 per liter of culture medium.

Once the culture medium is inoculated with a dose of the inoculant, it is incubated therein for an incubation period and at an incubation temperature sufficient to produce a sufficient amount (e.g., at least the CMC) of the biosurfactant of the present invention. For example, the incubation period is from about 12 hours to about 72 hours, preferably, from about 24 to about 48 hours and, most preferably, about 48 hours. In addition, for example, the incubation temperature is from about 15° C. to about 45° C., preferably, from about 20° C. to about 38° C.

After incubation of the inoculant at the incubation temperature for the prescribed incubation period, the incubated culture is sterilized, preferably, with humid heat. Other suitable sterilizing methods are known in the art and may be used. However, sterilizing with humid heat using steam under positive pressure, for example, from about 1 $kg/cm^2$ to about 1.5 $kg/cm^2$ (e.g., about 15 psig), is preferred at a sterilization temperature, preferably, of at least about 100° C. such as about 121° C., for a sterilization period, preferably, of at least about 10 minutes, more preferably, from 10 to about 35 minutes per liter of fluid to be sterilized. The aforesaid sterilization pressure, sterilization temperature and sterilization period may be varied so long as sterilization is achieved without substantially destroying the biosurfactant, its emulsifying or its viscosity-reducing capacity. Variations in sterilization procedures that are known in the art may be used without departing from the scope of the present invention.

In a first embodiment of the present invention, the aforesaid process for forming the biosurfactant of the present invention may be varied as noted below. For example, the sterilizing step may be modified wherein step (c) comprises the steps of:

(d) centrifuging the incubated culture at a centrifuging temperature for a centrifuging period to provide a supernatant layer;

(e) separating and then collecting the supernatant layer from the centrifuged culture; and (f) thereafter, sterilizing the supernatant layer.

Centrifuging the incubated culture may be achieved at any centrifuging speed, any centrifuging temperature and for any centrifuging period that is sufficient to separate out a supernatant layer from the incubated culture medium without substantially destroying or otherwise detrimentally affecting the biosurfactants' emulsifying or viscosity reducing capacity. However, a centrifuging speed, for example, from about 3,000 revolutions per minutes (rpm) to about 15,000 rpm may be used, preferably, from about 7,000 rpm to about 15,000 rpm and, most preferably, from about 10,000 rpm to about 11,000 rpm. Further, a centrifuging period from about 10 to about 20 minutes is preferred and about 15 minutes is most preferred. Also, a centrifuging temperature is, preferably, from about 0° C. to about 5° C. and, most preferably, from about 0° C. to about 4° C. After centrifuging, the supernatant is collected and then sterilized by the same procedure previously described.

In a second embodiment of the present invention, the process for forming the biosurfactant according to the present invention may be modified as indicated below. For example, the sterilizing step may be modified wherein step (f) comprises the steps of:

(g) adding a sufficient amount of an acid to the supernatant layer to yield the biosurfactant as a precipitate;

(h) separating and then collecting the precipitate from said supernatant layer;

(i) dissolving the precipitate in water to form an aqueous solution containing at least a critical micellar concentration of said biosurfactant; and (j) thereafter, sterilizing the aqueous solution with humid heat.

It is noted that a suitable acid for use in step (g) is any strong acid. Thus, for example, suitable acids may be selected from the group consisting of HCl, $H_2SO_4$ and mixtures thereof. Preferably, the acid is added in a stoichiometric amount to cause the precipitation of a salt form of the biosurfactant. For example, 0.91 ml of sulfuric acid may be added per liter of biosurfactant solution. Alternatively, 3.57 ml of hydrochloric acid may be added per liter of biosurfactant solution. Overall, approximately 1 ml of acid is added per 200 ml of supernatant. According to the present invention, step (g) provides the advantage of purifying the biosurfactant. While purification is not always necessary, it is sometimes preferred. Further, while other methods of purification known in the art may be used, precipitation with acid(s) is preferred due to its simplicity and cost effectiveness.

Step (h) is preferably carried out by centrifuging the precipitate at a centrifuging speed, for example, from about 7,000 rpm to about 15,000 rpm, preferably, from about 10,000 rpm to about 11,000 rpm. The centrifuging period and temperature is the same as that previously described with respect to step (d). The sterilizing step (j) is carried out in the same manner as previously indicated with respect to step (f).

After the biosurfactant is produced according to the procedure previously outlined, at least a critical micellar concentration of the biosurfactant is added to highly viscous hydrocarbons with water to form an emulsion wherein the emulsion has a viscosity of about 500 cp or less, preferably, about 100 cp or less at ambient or operating temperature (e.g., about 25° C.). The process for forming this low viscosity emulsion of the present invention comprises the steps of:

(a) providing a solution of a biosurfactant, said biosurfactant being present in at least a critical micellar concentration; and (b) mixing the solution with a high viscosity hydrocarbon having a viscosity between about 10,000 to about 500,000 cp at about 25° C., wherein the solution contains a sufficient amount of the biosurfactant to form a stable emulsion having a viscosity of less than or equal to about 500 cp at about 25° C.

As previously noted, typically, an emulsifying agent is used to form a condensed film around the droplets of the dispersed phase, the concentration of the emulsifier being sufficient for the task. Thus, while an inadequate concentration will not prevent coalescence, an excess of emulsifier above an optimum level achieves little in terms of increased stability of the emulsion. Potentially, an excess of an emulsifier may actually increase the viscosity of the emulsion. Apart from a possible increase in viscosity, there is little advantage in having a large excess of emulsifier. The excess may even result in undesirable effects such as excess foaming. The aim is to use the minimum amount of emulsifier consistent with producing a satisfactorily stable, low viscosity emulsion. Thus, it is preferred to use (1) a critical micellar concentration or (2) a minimum concentration above the critical micellar concentration of the biosurfactant. The concentration of the biosurfactant should be sufficient to provide a stable emulsion when combined with water and a highly viscous hydrocarbon (e.g., viscous crude oil having a viscosity from about 10,000 to about 500,000 cp at about 25° C.). Further, the stable emulsion should exhibit a viscosity of about 500 cp or less, preferably, about 100 cp or less at about 25° C. Even further, preferably, the stable emulsion should exhibit a reduced pressure drop of about 20 psi/mile or less.

Having described the invention, the following examples are given to illustrate specific applications and preferred embodiments of the invention. These specific examples are not intended to limit the scope of the invention described in this application.

EXAMPLES

According to the present invention, the following examples refer to emulsions of water, highly viscous crude oil and biosurfactant. The biosurfactant, a rhamnolipid compound of formula (I), supra, was produced by a strain of bacteria, *Pseudomonas aeruginosa,* denominated USB-CS1.

The viscosity measurements were made using a Rotational Viscosimeter (Haake™ RV2) fitted with a 500 kgf/m² viscosimeter head. The first step in making the viscosity measurement was to turn on the viscosimeter without the oil/water emulsion until a speed of 128 was reached. Thereafter, the viscosimeter was calibrated. Then, 8 ml of the oil/water emulsion was added to the viscosimeter for measuring emulsion viscosity. As recommended by the manufacturer, a constant acceleration rate of about 10 rpm/m was used. For viscosity measurements at temperature greater than ambient, a thermal bath was employed to ensure constant temperature.

For the test including accelerated heating, 100 ml of the oil/water emulsion was heated in an oven set at about 45° C. (or higher as needed). To measure the effects of temperature on emulsion stability and emulsion viscosity, the emulsion was heated to the desired temperature before any measurements were made. The viscosity measurements were made over a temperature range of about 25° C. to about 45° C. The viscosity measurements were made every 3 days on a 20 ml aliquot of the heated oil/water (63/35; w/w) emulsion. Measurements were made over a period of up to about 3 weeks.

Further, the emulsions were characterized by measuring the viscosity as a function of the storage time (e.g., 0 to 14 days), at a storage temperature of 25° C. or 45° C. at a viscosity measuring temperature of 25° C. or 50° C. In addition, the effect of accelerated heating from about 25° C. to about 80° C. over 2 hours on the viscosity emulsions was evaluated.

Figure 1A:
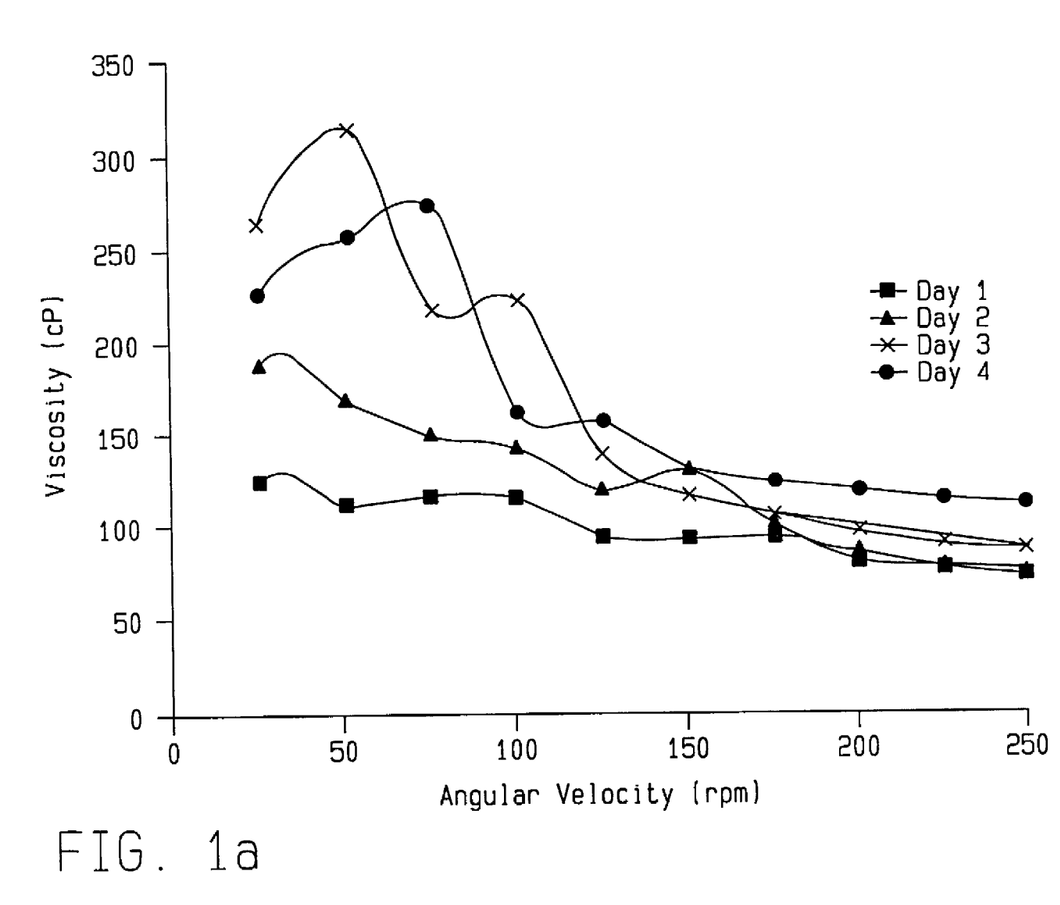
FIG. 1a is a plot of viscosity (in centipoise (cp)) versus angular velocity (revolutions per minute), for various storage times, of an emulsion (O/W=65/35; w/w) comprising a mixture of a highly viscous crude oil (about 10° API; heavy crude oil) and an aqueous emulsifying agent solution wherein the biosurfactant is produced by incubating *Pseudomonas aeruginosa* (USB-CS1) for an incubation period of 24 hours.

The effect of the incubation period of *Pseudomonas aeruginosa* (USB-CS1) culture on the viscosity is presented in FIGS. 1a (24 hours incubation period), 1b (48 hours incubation period) and 1c (72 hours incubation period). In each of FIGS. 1a, 1b and 1c, the viscosity was measured at days 1, 2, 3 and 4 after preparation of the emulsion, respectively.

EXAMPLE 1

The emulsions were prepared as indicated below. An aqueous biosurfactant solution was prepared by inoculating either (1) a rich commercial bacterial culture medium or (2) a define minimal culture medium (MMPB) with *Pseudomonas aeruginosa* (USB-CS1). The commercial bacterial culture medium contained nitrogen in its organic form from about 0.1% (w/v) to about 1% (w/v), enzymatic co-factor(s) from about 0.1% (w/v) to about 1% (w/v) and organic carbon from about 0.5% (w/v) to about 1.5% (w/v), respectively. Specifically, the culture medium contained glucose (1.5% w/v), yeast extract (0.5% w/v) and peptone (0.5% w/v).

The MMPB contained nitrogen (e.g., urea) from about 0.01% (w/v) to about 0.1% (w/v), $MgSO_4$ from about 0.0001% (w/v) to about 0.001% (w/v) and $K_2HPO_4$ from about 0.05% (w/v) to about 0.5% (w/v) (i.e., enzyme co-factor(s)) and organic carbon (e.g., glucose) from about 0.5% (w/v) to about 1.5% (w/v). Specifically, the MMPB contained glucose (1.5% w/v), urea (0.05% w/v), $MgSO_4$ (0.0005% w/v) and $K_2HPO_4$ (0.2% w/v).

The culture medium was inoculated with *Pseudomonas aeruginosa* (1% v/v; USB-CS1) under reciprocating agitation from about 80 to about 180 rpm. The mixture of the watery solution of inocule was continuously agitated in an axial reciprocal manner from about 100 to about 160 rpm for about 24 to about 72 hours, preferably, for about 24 hours. The inoculated culture medium was incubated at an incubation temperature from about 20°–38° C. for an incubation period from about 24 to about 72 hours to allow the microorganism to excrete the biosurfactant. After incubation, the culture medium was then either (1) directly sterilized, (2) centrifuged to collect a supernatant layer which was then sterilized or (3) centrifuged to collect a supernatant layer, the biosurfactant therein precipitated with acid, the precipitate collected and dissolved in water and then sterilized. The sterilization under all three options was carried out with humid heat (e.g., steam) in an autoclave under a positive pressure atmosphere from about 1 kg/cm² to about 1.5 kg/cm² (e.g., 15 psig) at a sterilization temperature of about 121° C. and for a sterilization period from about 10 to about 35 minutes per liter of fluid to be sterilized.

The sterilized biosurfactant-watery solution was mixed with viscous crude oil at about 25°–50° C. with a dynamic mixer set at a speed from about 1700 rpm to about 3000 rpm. The proportion of viscous crude oil to biosurfactant-watery solution was varied from about 50:50 (weight:weight) to about 80:20 (weight:weight). The stabilized emulsion was obtained by (1) weighing the aqueous biosurfactant solution, 80 mL, (2) adding crude oil and (3) mixing in the Helix dynamic mixer. The mixture was then degassified under vacuum at about 625 mm Hg pressure with a General Electric™ Model AC Engine 1725 vacuum pump for about 20 minutes. The degassified stable emulsion of the hydrocarbon (e.g., crude oil) in biosurfactant-watery solution exhibited a viscosity from about 100 cp to about 500 cp at about 25° C.

Figure 1B:
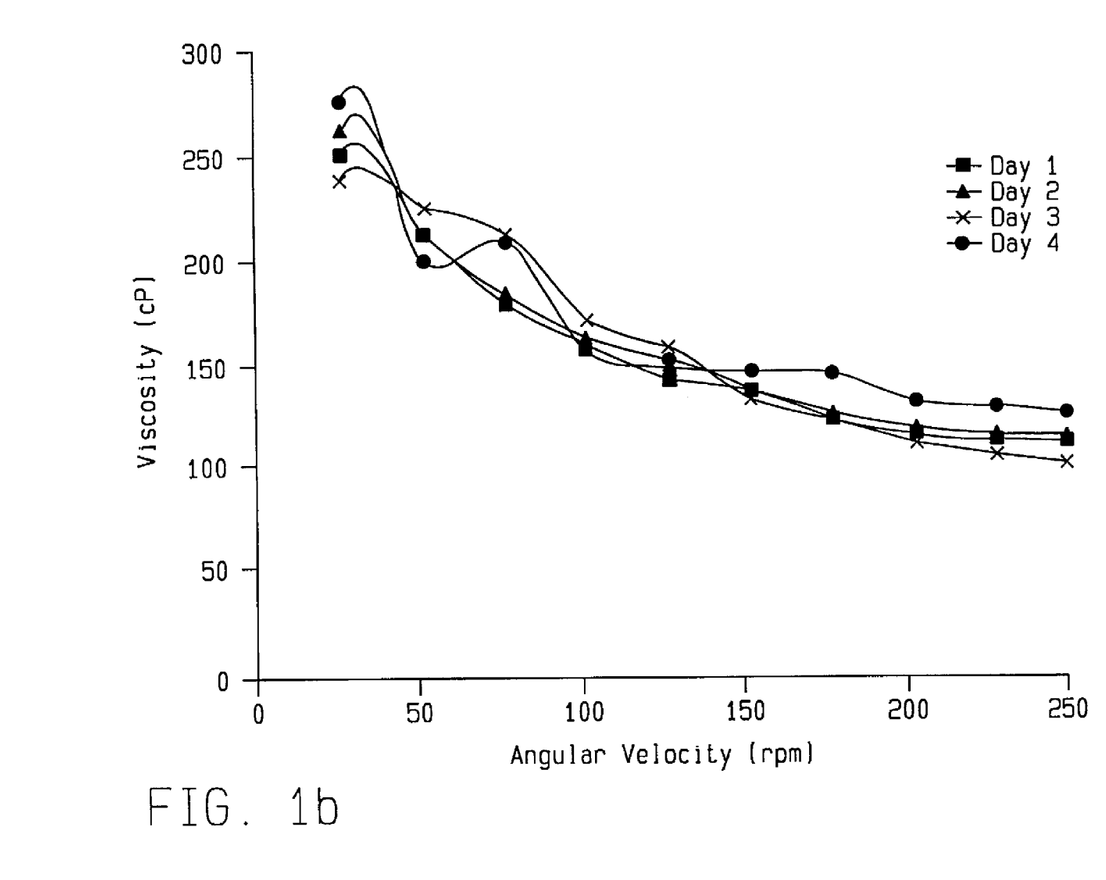
FIG. 1b is a plot of viscosity (in centipoise (cp)) versus angular velocity (revolution per minute), for various storage times, of an emulsion (O/W=65/35; w/w) comprising a mixture of a highly viscous crude oil (about 10° API; heavy crude oil) and an aqueous emulsifying agent solution wherein the biosurfactant is produced by incubating *Pseudomonas aeruginosa* (USB-CS1) for an incubation period of 48 hours.
Figure 1C:
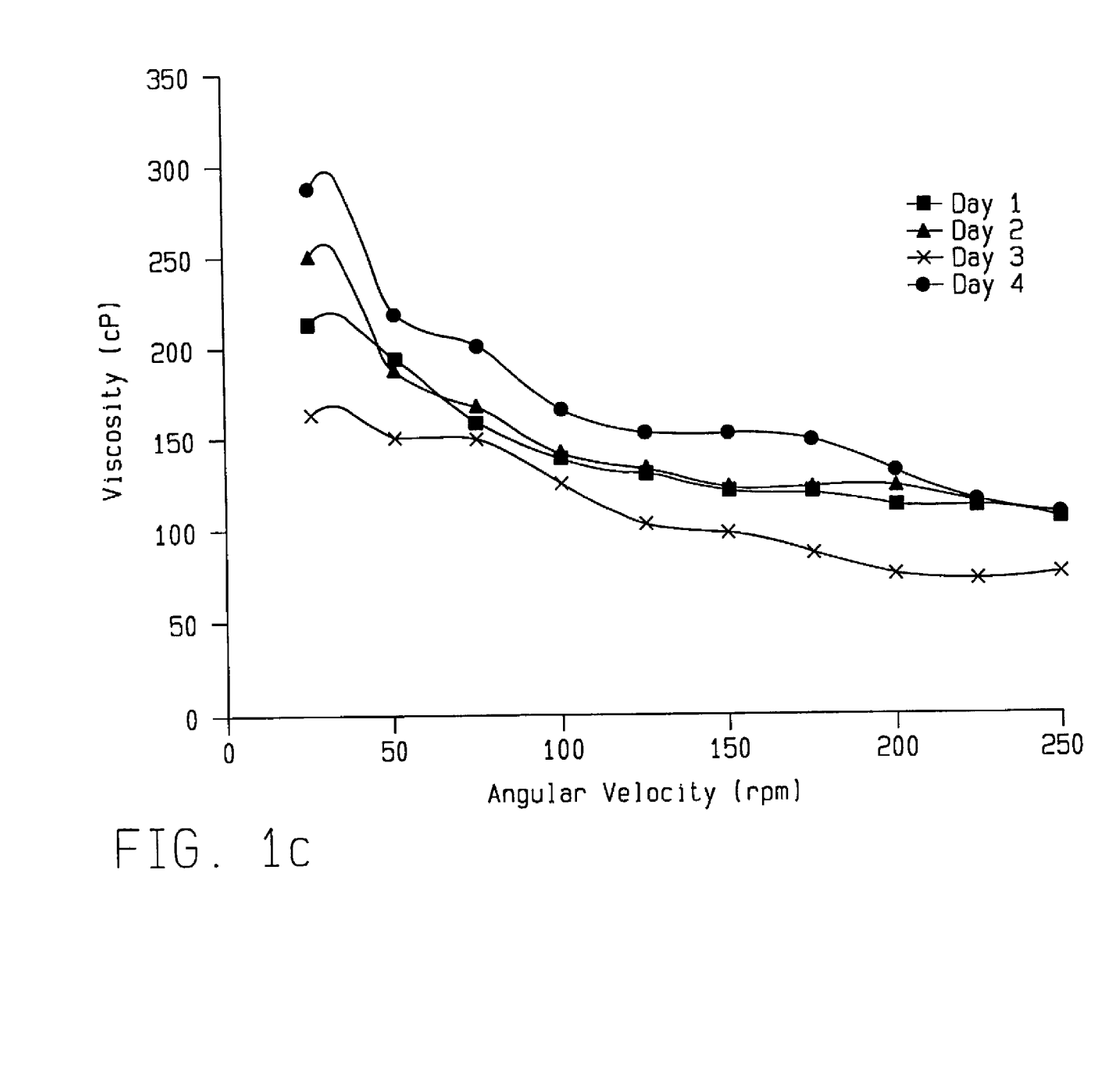
FIG. 1c is a plot of viscosity (in centipoise (cp)) versus angular velocity (revolutions per minute), for various storage times, of an emulsion (O/W=65/35; w/w) comprising a mixture of a highly viscous crude oil (about 10° API; heavy crude oil) and an aqueous emulsifying agent solution wherein the biosurfactant is produced by incubating *Pseudomonas aeruginosa* (USB-CS1) for an incubation period of 72 hours.

For FIGS. 1a, 1b and 1c, the viscosity measurements were made at 25° C. for emulsions prepared from a biosurfactant-watery solution and highly viscous crude oil (about 10° API) in a oil/water (O/W) proportion of 65/35 (w/w). It is apparent that the highest reproducibility in the behavior of the emulsions (i.e., with respect to viscosity) is observed for the biosurfactant-watery solution obtained after 48 hours of incubation period (i.e., FIG. 1b).

EXAMPLE 2

The stability of the emulsions formed using biosurfactant-watery solution (biosurfactant-watery solution formed after 48 hours of incubation period e.g., of *Pseudomonas aeruginosa*; USB-CS1) was evaluated for a 65/35 highly viscous crude oil (about 10° API) biosurfactant-watery emulsion (O/W) prepared at 25° C. according to the procedure of Example 1. The results are presented in FIGS. 2a and 2b. The following table (TABLE I) outlines some of the various conditions under which the emulsion stability was evaluated:

TABLE I

| VARIABLE | VALUE |
|---|---|
| Storage temperature | 25° C., 45° C. |
| Storage time | 3, 7, 10, 14 days after preparation |
| Temperature of the viscosity measurement | 25° C., 50° C. |
| Final temperature of accelerated heating for 2 hours | 40° C., 50° C., 60° C., 70° C. and 80° C. |

Figure 2A:
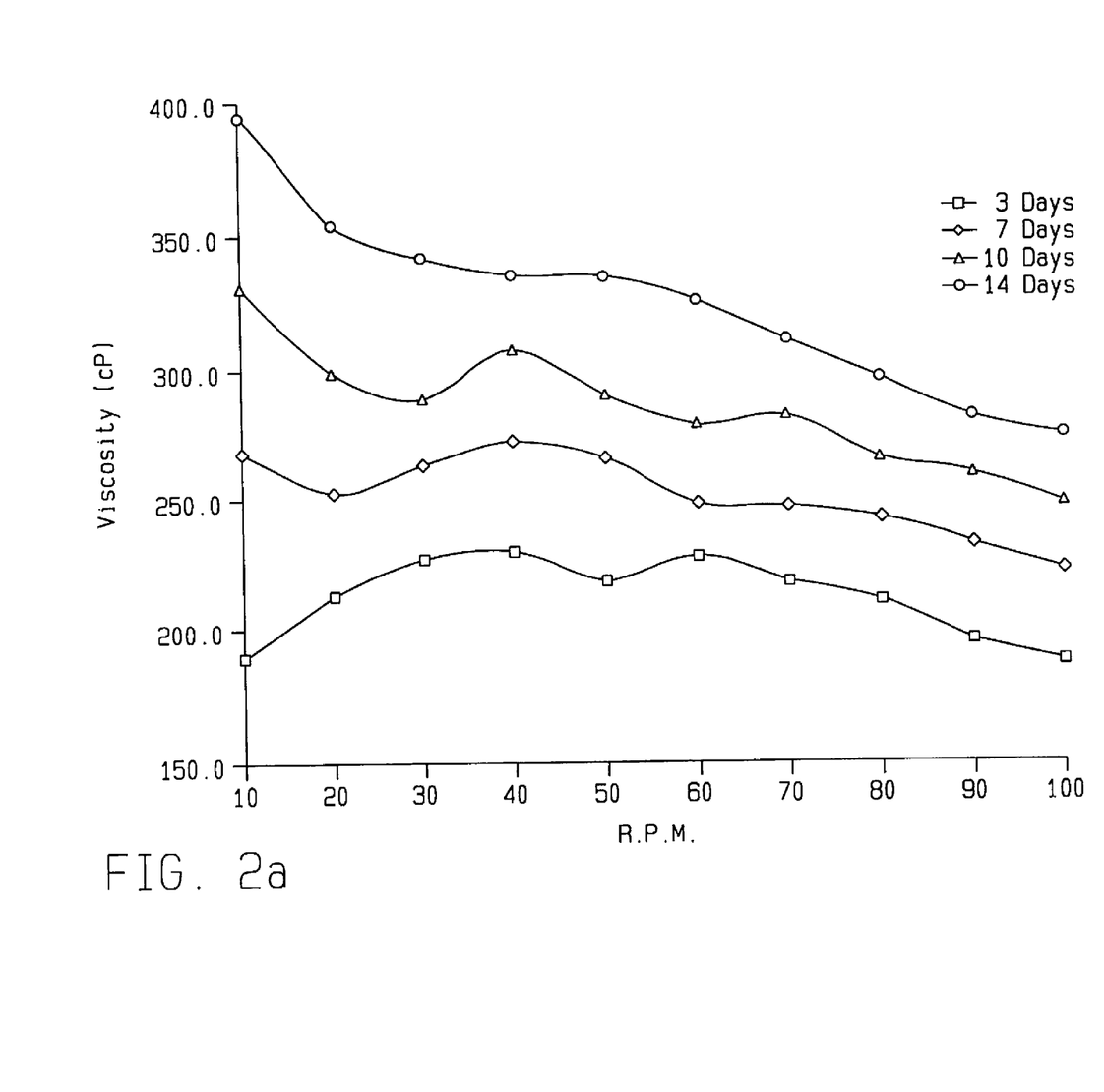
FIG. 2a is a plot of emulsion viscosity versus angular velocity for the emulsions made according to Example 2 stored at 25° C. for various storage times, the viscosity measurement temperature being 25° C. See TABLE I, infra.
Figure 2B:
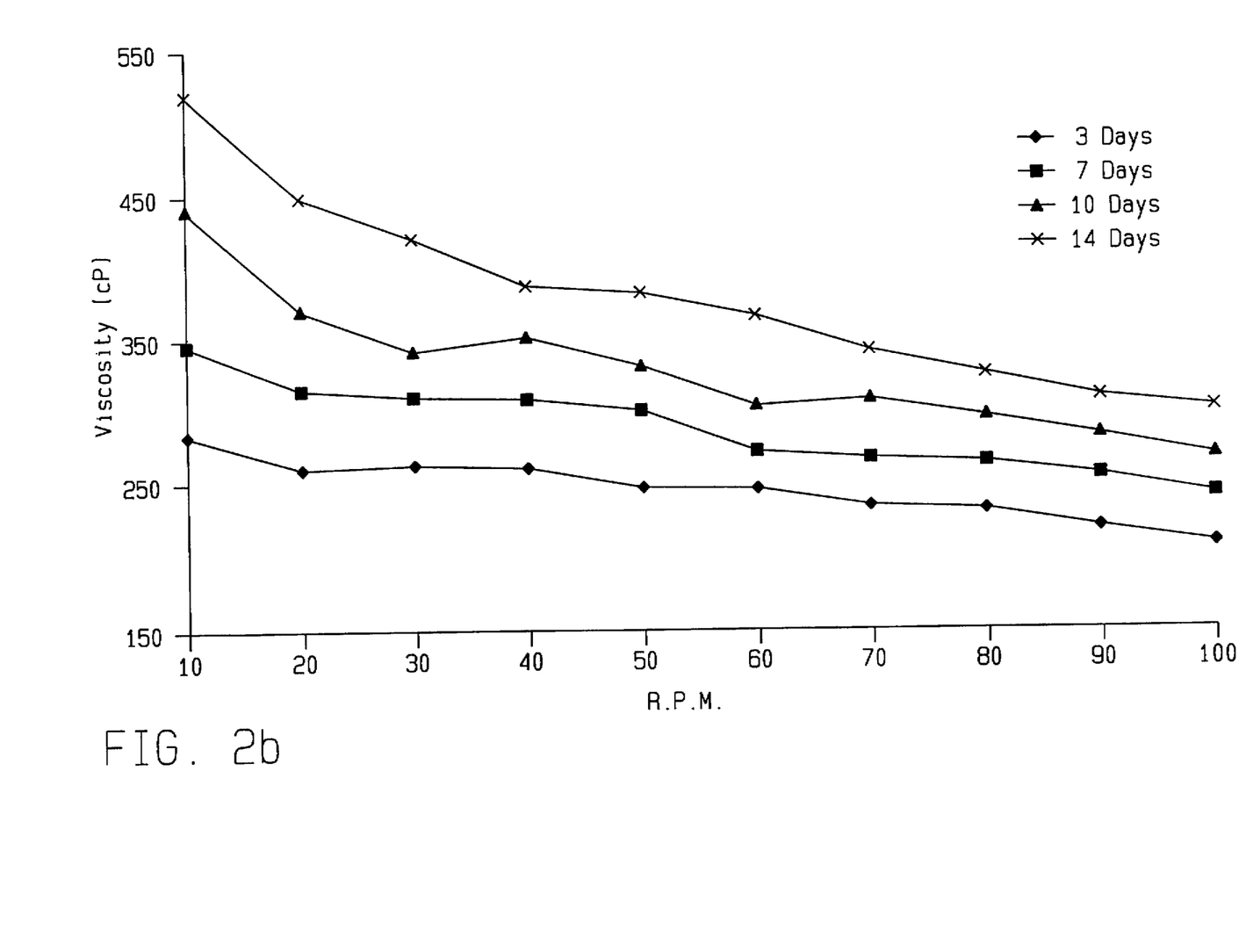
FIG. 2b is similar to FIG. 2a except that the storage temperature was 45° C.

FIGS. 2a (storage temperature of 25° C.) and 2b (storage temperature 45° C.) plot the effect of the variables noted in TABLE I versus viscosity. In all cases, there is an increase in viscosity with storage time. A maximum viscosity of about 340 cp is observed after 14 days of storage time at 25° C. at 50 rpm. A maximum viscosity of about 370 cp is observed after 14 days storage time at 45° C. at 50 rpm. In all cases, viscosity increases with storage temperature.

EXAMPLE 3

Figure 3:
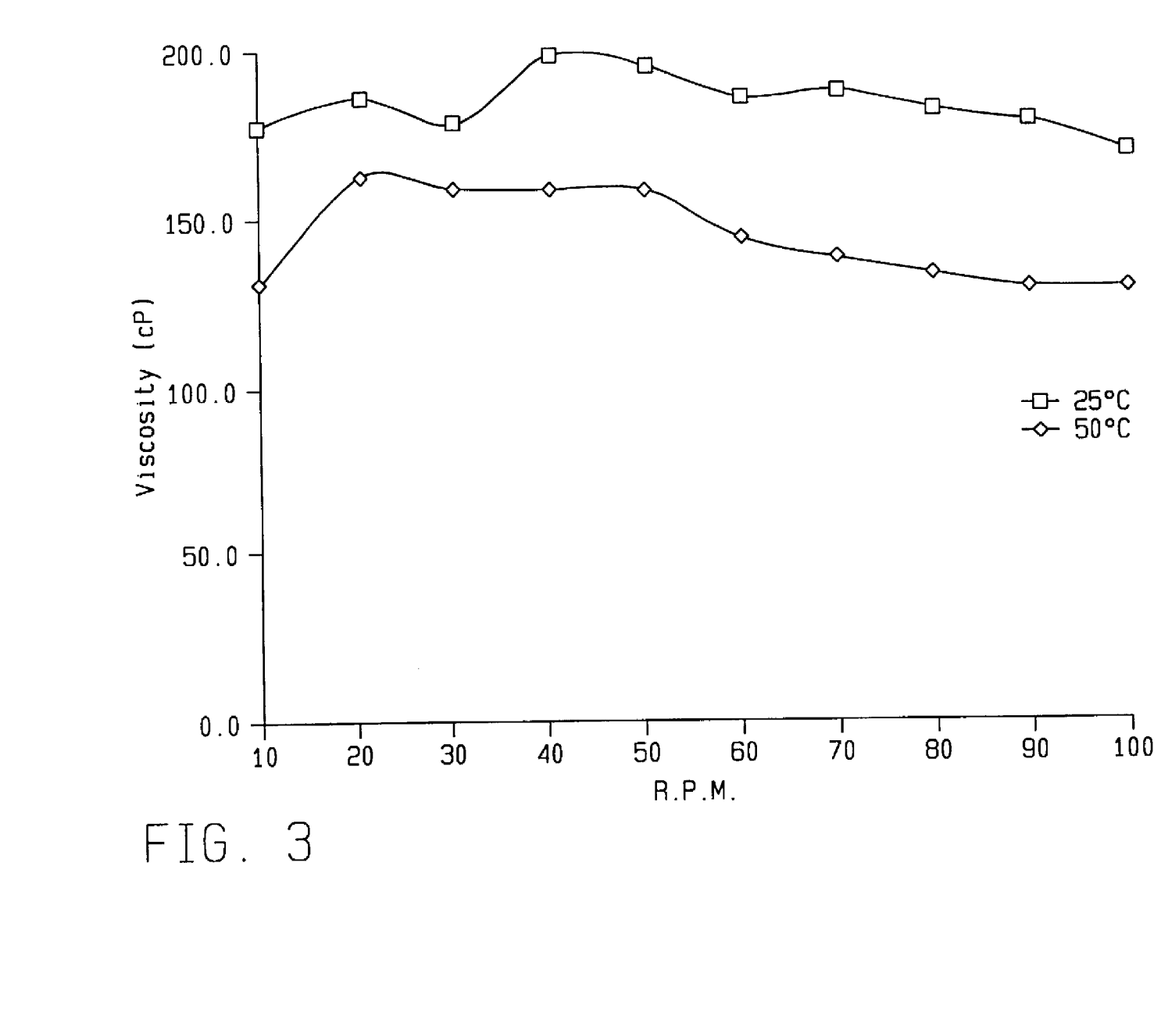
FIG. 3 is a plot of emulsion viscosity versus angular velocity for the emulsions made according to Example 3 wherein the viscosity was measured at 25° C. and 50° C., respectively.

FIG. 3 depicts the effect of the viscosity measurement temperature on the viscosity of the emulsion made with a *Pseudomonas aeruginosa* inoculate incubated for 48 hours. The O/W ratio was 65/35 (w/w) and the emulsion was prepared according to the procedure of Example 1. From FIG. 3, it is apparent that all viscosity measurements at 50° C. are lower than the measurements made at 25° C.

EXAMPLE 4

Figure 4A:
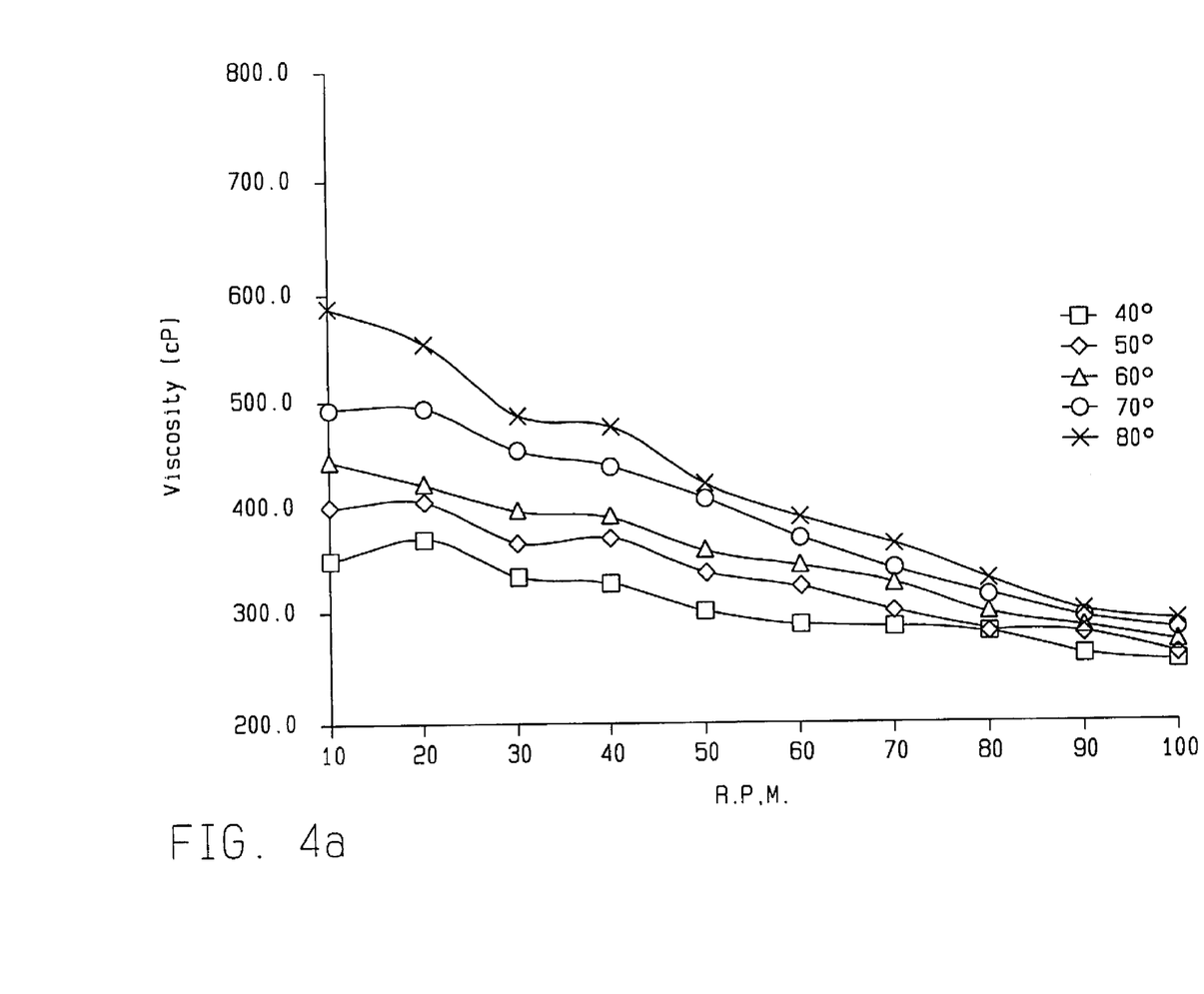
FIG. 4a is a plot of viscosity versus angular velocity for the emulsion made according to Example 4. The initial reading is taken at 25° C. immediately after preparation of the emulsion. The remainder of the data points are taken at different final heating temperatures achieved upon heating over about 2 hours (e.g., 40°, 50°, 60°, 70° and 80° C.).

FIG. 4a depicts the effect of accelerated heating on the viscosity of the emulsion made according to Example 1. The viscosity was measured at 25° C. An increase in the final heating temperature produced an increase in the viscosity of the emulsion. At 50 rpm, the viscosity is about 440 cp after heating to a final temperature of 80° C. during 2 hours.

EXAMPLE 5

Figure 4B:
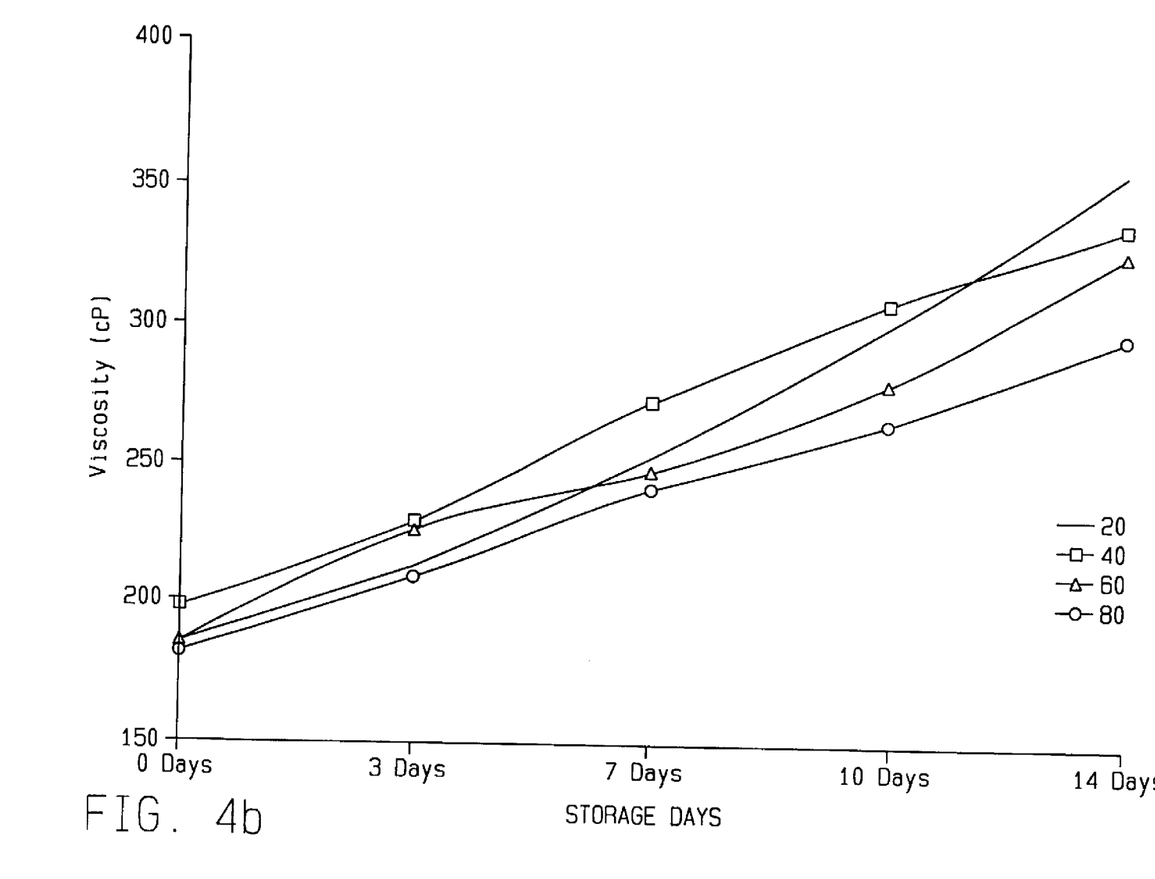
FIG. 4b is a plot of viscosity versus storage time for the emulsion made according to Example 5. The storage temperature is 25° C. The data points are taken at different final heating temperatures achieved upon heating over about 2 hours (e.g., 20° C., 40° C., 60° C. and 80° C.).

FIG. 4b depicts the effect of storage time and final accelerated heating temperature on the viscosity of the 65/35

O/W (w/w) emulsion made according to Example 1. A maximum viscosity of about 350 cp is measured at a final accelerated heating temperature of 80° C. at 100 rpm after 14 days storage time at 25° C.

EXAMPLE 6

An aqueous biosurfactant solution was prepared by inoculating *Pseudomonas aeruginosa* (USB-CS1) in a rich commercial bacterial culture medium or in a defined minimal medium (MMPB) (see, Example 1, supra) and incubating the inoculated culture at an incubation temperature from about 20° C. to about 38° C. with reciprocating agitation speed from about 80 to about 180 revolutions per minute (e.g. 100 to 160 rpm) during about 12 to about 72 hours. To obtain the aqueous biosurfactant solution, the incubated culture was (1) centrifuged to obtain a well-defined supernatant layer, (2) the supernatant layer was collected, (3) the biosurfactant of the supernatant layer was precipitated with acid (e.g., HCl) (4) the precipitate collected by filtration, (5) the precipitate dissolved in water and (5) the aqueous biosurfactant solution sterilized with humid heat (e.g., steam) in a positive pressure atmosphere between about 1 to about 1.5 Kg/cm$^2$ (e.g., 15 psig) for about 10 to about 35 minutes (e.g., 15 minutes) per liter of fluid.

The aqueous biosurfactant solution was then mixed with highly viscous crude oil at about 25°–50° C. with a dynamic mixer at a speed from about 1700 to about 3000 rpm. The proportion of the oil to aqueous biosurfactant solution was from about 50:50 to about 70:30 (i.e., oil:water; w/w). A stable emulsion of the oil to water was obtained with a viscosity of between about 100 to about 500 centipoise measured at about 25° C. after degassifying the emulsion.

EXAMPLE 7

Extraction of viscous crude oil can be carried out as prophetically described below. First, a culture inoculated with *Pseudomonas aeruginosa* (USB-CS1) is injected near crude oil reservoir porosities. Second, water is injected below the oil reservoir. It is expected that the USB-CS1 will produce and excrete biosurfactant to emulsify and reduce the viscosity of the oil contained in the reservoir. It is further expected that the oxidative process of *P. aeruginosa* USB-CS1 will also generate $CO_2$ which will aid in the extraction of the oil from the reservoir. The exact procedural steps for injecting USB-CS1 and water into the oil reservoir are well known to those skilled in the art to which the present invention pertains.

Other objects, features and advantages of the invention will be readily apparent to those skilled in the art from the description of certain preferred embodiments thereof, taken in conjunction with the accompanying examples, although variations and modifications may be effected without departing from the scope and spirit of the novel concepts of the claimed invention.

What is claimed is:

1. A storage-stable oil-in water emulsion comprising:
   a high viscosity hydrocarbon oil having a viscosity between about 10,000 cp to about 500,000 cp at about 25° C.; and
   an aqueous solution of a biosurfactant comprising a rhamnolipid in a concentration sufficient to form an emulsion;
   wherein the emulsion has a viscosity of less than about 500 cp when measured at 25° C. at between 10 and 100 rpm after 14 days storage at about 25° C., and a weight ratio of oil to water from about 50:50 to about 80:20.

2. The emulsion of claim 1 wherein the rhamnolipid has a structure of formula (I):

wherein or mixtures thereof, wherein n, m, p and q are integers and wherein A$^+$ is a cation or H.

3. The emulsion of claim 2, wherein n=6, p=6, m=1 and q=1.

4. The emulsion of claim 2, wherein the emulsion has a viscosity of less than or equal to about 100 cp at about 25° C. and a weight ratio of oil to water from about 65:35 to about 70:30.

5. A storage-stable oil-in-water emulsion comprising:
   a high viscosity hydrocarbon oil having a viscosity between about 10,000 cp to about 500,000 cp at about 25° C.; and
   an aqueous solution of a biosurfactant comprising a rhamnolipid in a critical micellar concentration to form an emulsion;
   wherein the emulsion has a viscosity of less than about 500 cp when measured at 25° C. at between 10 and 100 rpm after 14 days storage at about 25° C., a weight ratio of oil to water from about 50:50 to about 80:20, and is made by a process which comprises:
   (a) forming the rhamnolipid biosurfactant by:
      inoculating a culture medium containing nitrogen, an enzyme co-factor and an organic carbon source with a does of inoculant containing a biosurfactant producing microorganism of a strain of *Pseudomonas aeruginosa*;
      incubating said microorganism in said culture for an incubation period at an incubation temperature sufficient to produce an incubated culture; and
      sterilizing said incubated culture with heat at a sterilization temperature for a sterilization period to form the rhamnolipid biosurfactant in an aqueous solution; and
   (b) forming the oil-in-water emulsion by:
      mixing said hydrocarbon oil with said rhamnolipid biosurfactant containing aqueous solution in amounts sufficient to provide the emulsion with a weight ratio of oil to water of from about 50:50 to about 80:20; and
      degassifying said emulsion to form said storage-stable oil-in-water emulsion.

6. The emulsion of claim 5 wherein the process further comprises mixing the hydrocarbon oil with the aqueous solution at a temperature of between about 25° and 50° C.

7. The emulsion of claim 5 wherein the degassifying step is carried out at a vacuum of less than about 625 mm Hg for at least about 20 minutes.

8. The emulsion of claim 5 wherein the process further comprises selecting said dose of inoculant is from about 0.1% (v/v) to about 9% (v/v) based on a total volume of said culture medium.

9. The emulsion of claim 8 wherein the process further comprises further comprises providing in the culture medium said nitrogen in the form of urea in an amount from about 0.01% (w/v) to about 0.1% (w/v) based on a total volume of the culture medium.

10. The emulsion of claim 8 wherein the process further comprises providing in the culture medium said nitrogen in the form of peptone, yeast extract or a mixture thereof wherein said peptone, said yeast extract or said mixture thereof is present in an amount from about 0.05% (w/v) to about 1.5% (w/v) based on a total volume of said culture medium.

11. The emulsion of claim 8 wherein the process further comprises providing in the culture medium said enzyme co-factor being selected from the group consisting of $Mg^{++}$ ions, phosphorous and mixtures thereof.

12. The emulsion of claim 11 wherein the process further comprises providing in the culture medium said $Mg^{++}$ ions as $MgSO_4$ which is present in an amount from about 0.0001% (w/v) to about 0.01% (w/v) and providing said phosphorous as $K_2HPO_4$ in an amount from 0.05% (w/v) to about 0.5% (w/v) based on a total volume of said culture medium.

13. The emulsion of claim 11, wherein the process further comprises providing in the culture medium said organic carbon by adding a material which is different than said nitrogen source and which organic carbon is peptone, yeast, glucose or a mixture thereof.

14. The emulsion of claim 13 wherein the process further comprises providing said glucose in said culture medium in an amount from about 0.5% (w/v) to about 1.5% (w/v) based on a total volume of said culture medium.

15. The emulsion of claim 11 wherein the process further comprises providing said nitrogen source and said organic carbon in said culture medium in the form of peptone, yeast or mixtures thereof.

16. The emulsion of claim 5 wherein the process further comprises selecting said incubation period to be from about 12 hours to about 72 hours, selecting said incubation temperature to be from about 15° C. to about 45° C. and selecting steam under positive pressure as a source of said humid heat.

17. The emulsion of claim 16 wherein the process further comprises selecting said positive pressure to be from about 1.0 kg/cm² to about 1.5 kg/cm², selecting said sterilization period to be from about 10 to about 35 minutes per liter of said incubated culture and selecting said incubation temperature to be from about 20° C. to about 38° C.

18. The emulsion of claim 17 wherein the process further comprises isolating the rhamnolipid biosurfactant from the culture medium prior to forming the aqueous solution, and providing said aqueous solution in a concentration sufficient to form said stable emulsion with a viscosity of about 100 cp or less at about 25° C.

19. The emulsion of claim 5 wherein the process further comprises selecting said hydrocarbon oil to have an American Petroleum Index of 13 degrees or less, and adding water to said oil in an amount sufficient to provide said emulsion with a weight ratio of oil to water of from about 65:35 to about 70:30.

20. The emulsion of claim 5 wherein the process further comprises:
centrifuging said incubated culture at a first centrifuging temperature for a first centrifuging period and at a first centrifuging speed to provide a supernatant layer;
separating and then collecting said supernatant layer from the centrifuged culture; and
thereafter, sterilizing said supernatant layer at said sterilization temperature for said sterilization period.

21. The emulsion of claim 20 wherein the process further comprises selecting said first centrifuging temperature to be from about 0° C. to about 5° C., selecting said first centrifuging period to be from about 10 minutes to about 20 minutes and selecting said first centrifuging speed to be from about 3,000 rpm to about 15,000 rpm.

22. The emulsion of claim 21 wherein the process further comprises:
adding a sufficient amount of an acid to said supernatant layer to yield said rhamnolipid biosurfactant as a precipitate;
separating and then collecting said precipitate from said supernatant layer;
dissolving said precipitate in water to form an aqueous solution containing at least said critical micellar concentration of said rhamnolipid biosurfactant; and
thereafter, sterilizing said aqueous solution with humid heat said sterilization temperature for said sterilization period.

23. The emulsion of claim 22 wherein the process further comprises centrifuging said supernatant layer containing said precipitate at a second centrifuging temperature for a second centrifuging period and at a second centrifuging speed and removing the centrifuged precipitate from said supernatant layer.

24. The emulsion of claim 23 wherein the process further comprises selecting said second centrifuging temperature to be from about 0° C. to about 5° C., selecting said second centrifuging period to be from about 10 minutes to about 20 minutes and selecting said second centrifuging speed to be from about 7,000 rpm to about 15,000 rpm.

25. The emulsion of claim 24 wherein the process further comprises selecting said acid from the group consisting of HCl, $H_2SO_4$ and mixtures thereof.

26. The emulsion of claim 1 wherein the maximum viscosity is less than about 400 cp.

27. The emulsion of claim 5 wherein the maximum viscosity is less than about 400 cp.

28. The emulsion of claim 1 wherein the rhamnolipid biosurfactant is produced by *Pseudomonas aeruginosa*.

29. The emulsion of claim 1 wherein the rhamnolipid biosurfactant is produced by *Pseudomonas aeruginosa* ATCC 55925 (USB-CS1).

30. The emulsion of claim 5 wherein the rhamnolipid biosurfactant is produced by *Pseudomonas aeruginosa* ATCC 55925 (USB-CS1).

* * * * *

UNITED STATES PATENT AND TRADEMARK OFFICE
CERTIFICATE OF CORRECTION

PATENT NO. : 5,866,376

DATED : February 2, 1999

INVENTORS : Carlos Ali ROCHA et al.

It is certified that error appears in the above-identified patent and that said Letters Patent is hereby corrected as shown below:

Column 14, line 44 (claim 5, line 16): change "does" to --dose--.

Signed and Sealed this

Fifteenth Day of June, 1999

Attest:

Q. TODD DICKINSON

*Attesting Officer*    *Acting Commissioner of Patents and Trademarks*